(12) United States Patent
Nakamura et al.

(10) Patent No.: US 10,083,503 B2
(45) Date of Patent: Sep. 25, 2018

(54) IMAGE AREA SPECIFICATION DEVICE AND METHOD, AND X-RAY IMAGE PROCESSING DEVICE AND METHOD

(71) Applicant: FUJIFILM Corporation, Tokyo (JP)

(72) Inventors: Keigo Nakamura, Ashigarakami-gun (JP); Tomoyuki Takahashi, Ashigarakami-gun (JP)

(73) Assignee: FUJIFILM Corporation, Minato-ku, Tokyo (JP)

( * ) Notice: Subject to any disclaimer, the term of this patent is extended or adjusted under 35 U.S.C. 154(b) by 19 days.

(21) Appl. No.: 15/051,883

(22) Filed: Feb. 24, 2016

(65) Prior Publication Data

US 2016/0171691 A1    Jun. 16, 2016

Related U.S. Application Data

(63) Continuation of application No. PCT/JP2014/004313, filed on Aug. 21, 2014.

(30) Foreign Application Priority Data

Aug. 27, 2013 (JP) .................................. 2013-175219

(51) Int. Cl.
*G06K 9/00* (2006.01)
*G06T 7/00* (2017.01)
*A61B 6/00* (2006.01)
*G06K 9/46* (2006.01)
(Continued)

(52) U.S. Cl.
CPC ............ *G06T 7/0012* (2013.01); *A61B 6/505* (2013.01); *A61B 6/5211* (2013.01); *G06K 9/4604* (2013.01); *G06T 5/009* (2013.01); *G06T 5/40* (2013.01); *G06T 2207/10116* (2013.01);
(Continued)

(58) Field of Classification Search
None
See application file for complete search history.

(56) References Cited

U.S. PATENT DOCUMENTS 6,141,437 A * 10/2000 Xu .................... G06T 7/0012
128/922
8,121,373 B2 * 2/2012 Matsumoto ........... G06T 7/0012
382/128
(Continued)

FOREIGN PATENT DOCUMENTS

JP          6-61325 B2     8/1994
JP          7-38758 A      2/1995
(Continued)

OTHER PUBLICATIONS

International Searching Authority, Written Opinion for PCT/JP2014/004313 dated Dec. 16, 2014. [PCT/ISA/237].
(Continued)

*Primary Examiner* — Nancy Bitar
(74) *Attorney, Agent, or Firm* — Sughrue Mion, PLLC

(57) ABSTRACT

A partial region extraction unit extracts a partial region including a distal portion in the vicinity of a boundary between a subject region including the distal portion and a void region from a radiological image including the distal portion of the human body. A designation region determination unit determines at least one of the void region and the partial region as a designation region for designating the partial region.

10 Claims, 7 Drawing Sheets

(51) Int. Cl.
    *G06T 5/00* (2006.01)
    *G06T 5/40* (2006.01)
(52) U.S. Cl.
    CPC ............... *G06T 2207/20008* (2013.01); *G06T 2207/30008* (2013.01)

(56) References Cited

U.S. PATENT DOCUMENTS

| | | | | |
|---|---|---|---|---|
| 8,687,864 | B2* | 4/2014 | Matsumoto | G06T 7/0012 |
| | | | | 382/128 |
| 8,805,471 | B2* | 8/2014 | Sakuragi | G06T 7/0012 |
| | | | | 600/407 |
| 9,824,445 | B2* | 11/2017 | Akimoto | G06T 7/11 |
| 2003/0215120 | A1* | 11/2003 | Uppaluri | A61B 6/482 |
| | | | | 382/128 |
| 2004/0151358 | A1* | 8/2004 | Yanagita | G06F 19/321 |
| | | | | 382/132 |
| 2005/0135665 | A1* | 6/2005 | Shinbata | G06T 5/004 |
| | | | | 382/132 |
| 2008/0262341 | A1* | 10/2008 | Boyden | A61F 2/02 |
| | | | | 600/424 |
| 2009/0129679 | A1* | 5/2009 | Miyamoto | G06K 9/4647 |
| | | | | 382/190 |
| 2009/0136110 | A1 | 5/2009 | Kaji | |

FOREIGN PATENT DOCUMENTS

| | | |
|---|---|---|
| JP | 8-331385 A | 12/1996 |
| JP | 2000-155838 A | 6/2000 |
| JP | 2000-316836 A | 11/2000 |
| JP | 2004-364336 A | 12/2004 |
| JP | 4844560 B2 | 12/2011 |

OTHER PUBLICATIONS

International Search Report for PCT/JP2014/004313 dated Dec. 16, 2014.

* cited by examiner

IMAGE AREA SPECIFICATION DEVICE AND METHOD, AND X-RAY IMAGE PROCESSING DEVICE AND METHOD

CROSS REFERENCE TO RELATED APPLICATIONS

The present application is a Continuation of PCT International Application No. PCT/JP2014/004313 filed on Aug. 21, 2014, which claims priority under 35 U.S.C. § 119(a) to Japanese Patent Application No. 2013-175219 filed on Aug. 27, 2013. Each of the above applications is hereby expressly incorporated by reference, in its entirety, into the present application.

BACKGROUND OF THE INVENTION

1. Field of the Invention

The present invention relates to an image region designation device and method which designates a necessary region in a radiological image and a radiological image processing device and method which performs a gradation process for a radiological image.

2. Description of the Related Art

A radiological image used in an image diagnosis is acquired by an imaging process of a computed radiography (CR) system or an imaging process using a radiation detector (FPD). The dynamic range of the acquired radiological image is very wide. When the entire dynamic range of the radiological image with a wide dynamic range is converted into an image, the contrast of the image is reduced and is not suitable for diagnosis. Therefore, image processing, such as a gradation process or a frequency enhancement process, is performed in order to adjust the dynamic range of the radiological image such that the concentration and contrast of the image to be displayed are appropriate. As a gradation processing method, for example, a method has been proposed which calculates a histogram of the pixel values of a radiological image, switches an algorithm or parameters on the basis of supplementary information, such as a captured part of the radiological image, an imaging direction, and the age of a subject, creates a portion (main histogram) corresponding to a main region of the histogram, and allocates a gradation curve such that the concentration range of the main histogram falls in the dynamic range of a display device. In addition, a method has been proposed which sets a region of interest (ROI) in a featured region of a radiological image, switches an algorithm or parameters on the basis of supplementary information of the radiological image, and allocates a gradation curve such that a reference value (for example, a maximum value or a median value) of the pixel value in the ROI is a predetermined concentration (for example, JP1994-61325B (JP-H06-61325B)).

However, in the above-mentioned method, since the supplementary information, such as the captured part of the radiological image, the imaging direction, and the age of the subject, is required, it is necessary to input the supplementary information of the radiological image to an image processing device which performs image processing whenever a radiological image is captured. Here, the operator who performs an imaging operation selects an imaging menu in the image processing device and inputs the supplementary information. For example, in general, about 100 to 300 imaging menus are used and the number of imaging menus varies depending on facilities. Therefore, the operation of selecting a desired imaging menu is very complicated depending on the operator who performs an imaging operation, which is likely to cause an input error. In addition, it is necessary to set optimal image processing parameters in each imaging menu in order to perform optimal image processing and an adjustment operation for setting the parameters is also very complicated. Furthermore, a radiology information system (hereinafter, referred to as a RIS) is introduced to allocate an imaging menu to imaging order information. In this case, it is not necessary to perform an imaging menu input operation. However, in the case of facilities without a RIS, the operator needs to perform the imaging menu input operation whenever an imaging operation is performed.

A large hospital has a full-time operator who is in charge of image processing. Therefore, when the quality of a radiological image is not satisfied, it is easy to correct the radiological image. However, it is difficult for a small hospital to employ the full-time operator who is in charge of image processing and it is very difficult to correct the radiological image such that the same quality as that obtained by the full-time operator who is in charge of image processing is obtained. Therefore, it is preferable to provide an image processing device which can automatically convert an image so as to be suitable for diagnosis, regardless of a subject or imaging conditions (for example, a tube voltage, a dose, and positioning).

JP4844560B, JP2004-364336A, and JP1996-331385A (JP-H08-331385A) disclose a method which extracts a region of interest from a radiological image and converts the gradation of the radiological image such that the concentration of the extracted region is a desired value. The method disclosed in JP4844560B extracts the bone part or the soft part included in a radiological image as the region of interest, weights the extracted region of interest to generate a weighted image, multiplies the radiological image by the weighted image to create a weighted histogram, evaluates the weighted histogram using a predetermined evaluation function, calculates a shift value of the histogram at which the evaluation value is the maximum, and determines image processing conditions in which a predetermined processing result is obtained at a pixel value of the radiological image corresponding to the maximum value of the evaluation function where the shift value is obtained, particularly, image processing conditions in which the pixel value corresponding to the shift value is a desired concentration value. The method disclosed in JP4844560B extracts the region of interest from the image, without using the supplementary information of the image and determines the image processing conditions for each image on the basis of the extracted region. Therefore, it is possible to obtain a radiological image subjected to the gradation process, without inputting an imaging menu.

SUMMARY OF THE INVENTION

In the method disclosed in JP4844560B, the bone part or the soft part is automatically extracted as the region of interest. However, it is difficult to accurately extract the bone part region or the soft part region in a distal portion of the human body, such as the patella, the nasal bone, a hand, a foot, or a finger. As a result, it is difficult to allocate an optimal gradation curve and it is necessary to readjust the region.

When the region needs to be readjusted, for example, the operator who performs an imaging operation sets the region of interest in an attention region of the radiological image. The distal portion of the human body is adjacent to a void region corresponding to a region which has been directly irradiated with radiation in the radiological image. Therefore, when the soft part region or the bone part region of the distal portion is designated, there is a concern that the void region will be erroneously designated or the bone part will be erroneously designated instead of the intended soft part. In particular, when a terminal with a small touch panel screen, such as a tablet computer, is used, it is difficult to accurately designate only the desired distal portion. As such, when it is difficult to accurately designate the desired distal portion, the optimal gradation process is performed for an erroneously designated region. As a result, the concentration and contrast of the radiological image subjected to the gradation process are not suitable for diagnosis.

The invention has been made in view of the above-mentioned problems and an object of the invention is to provide a technique which can accurately designate a desired distal portion particularly in a radiological image including a distal portion of the human body.

According to an aspect of the invention, there is provided an image region designation device that designates a region in a radiological image including a distal portion of a human body. The image region designation device includes: partial region extraction means for extracting a partial region including the distal portion in the vicinity of a boundary between a subject region including the distal portion and a void region from the radiological image; and designation region determination means for determining at least one of the void region and the partial region as a designation region for designating the partial region.

The "void region" means a high-concentration region obtained by the direct emission of radiation to, for example, a radiation detector for detecting radiation.

In the image region designation device according to the above-mentioned aspect of the invention, the designation region determination means may determine the void region and the partial region as the designation region.

In the image region designation device according to the above-mentioned aspect of the invention, the designation region determination means may determine the void region as the designation region.

In the image region designation device according to the above-mentioned aspect of the invention, the partial region extraction means may include: first extraction means for extracting at least one of the subject region and the void region from the radiological image; and second extraction means for extracting the partial region on the basis of at least one of the subject region and the void region.

According to another aspect of the invention, there is provided a radiological image processing device including: the image region designation device according to the above-mentioned aspect of the invention; input means for receiving the designation region; feature amount calculation means for calculating a feature amount which is concentration of the radiological image on the basis of the partial region when the designation region is designated; target concentration calculation means for calculating a target concentration which is converted from the feature amount; and image processing means for performing image processing including a gradation process for the radiological image such that the feature amount is the target concentration.

The radiological image processing device according to the above-mentioned aspect of the invention may further include anatomic region extraction means for extracting a bone part region or a soft part region included in the radiological image as an anatomic region from the partial region. The feature amount calculation means may calculate the feature amount on the basis of the bone part region or the soft part region.

In the radiological image processing device according to the above-mentioned aspect of the invention, the target concentration calculation means may calculate the target concentration on the basis of the radiological image.

According to still another aspect of the invention, there is provided an image region designation method that designates a region in a radiological image including a distal portion of a human body. The image region designation method includes: extracting a partial region including the distal portion in the vicinity of a boundary between a subject region including the distal portion and a void region from the radiological image; and determining at least one of the void region and the partial region as a designation region for designating the partial region.

According to yet another aspect of the invention, there is provided a radiological image processing method including: receiving the designation region determined by the image region designation method according to the above-mentioned aspect of the invention; calculating a feature amount which is concentration of the radiological image on the basis of the partial region when the designation region is designated; calculating a target concentration which is converted from the feature amount; and performing image processing including a gradation process for the radiological image such that the feature amount is the target concentration.

A program may be provided which causes a computer to perform the image region designation method and the radiological image processing method according to the invention.

According to the image region designation device and method of the invention, the partial region including the distal portion in the vicinity of the boundary between the subject region and the void region is extracted, and at least one of the void region and the partial region is determined as the designation region for designating the partial region. Therefore, it is possible to designate the partial region including the distal portion, using the designation region that is wider than the distal portion. As a result, when a desired distal portion is designated, it is possible to prevent another region from being erroneously designated and thus to accurately designate the desired distal portion.

In the radiological image having a distal portion as a subject, the size of the void region is large. Therefore, when the void region and the partial region, or the void region is determined as the designation region, it is possible to designate the partial region, using the region that is wider than the distal portion. As a result, it is possible to accurately and easily designate a desired distal portion.

According to the radiological image processing device and method of the invention, when the designation region is designated, a feature amount which is concentration of the radiological image is calculated on the basis of the partial region including the distal portion, the target concentration which is converted from the feature amount is calculated, and image processing including a gradation process is performed for the radiological image such that the feature amount is the target concentration. Therefore, it is not necessary to set an imaging menu in detail. As a result, it is possible to optimize the quality of the processed radiological image including the distal portion while reducing the number of imaging menus to be set.

DESCRIPTION OF THE PREFERRED EMBODIMENTS

Figure 1:
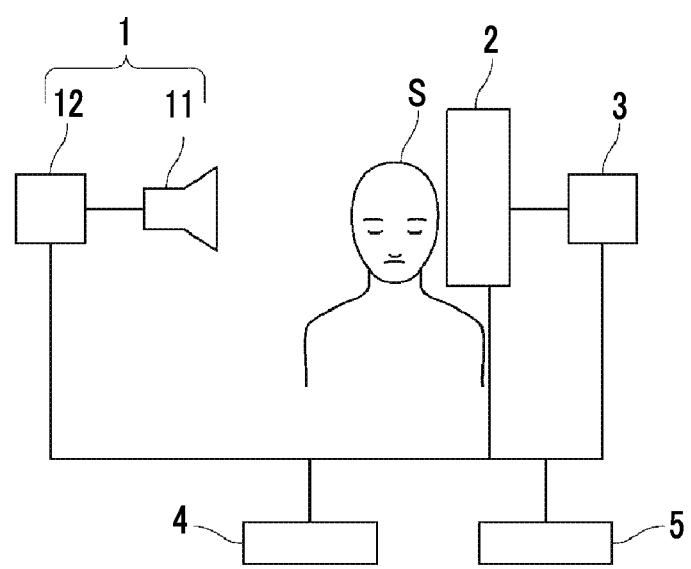
FIG. 1 is a block diagram schematically illustrating the structure of a radiological image diagnosis system to which an image region designation device and a radiological image processing device according to embodiments of the invention are applied.

Hereinafter, embodiments of the invention will be described with reference to the drawings. FIG. 1 is a block diagram schematically illustrating the structure of a radiological image diagnosis system to which an image region designation device and a radiological image processing device according to the invention are applied. As illustrated in FIG. 1, the radiological image diagnosis system includes a radiation generation device 1, a radiation detector 2, a radiological image processing device 3, an imaging control device 4, and an input unit 5. The radiation generation device 1 and the radiation detector 2 are arranged so as to face each other, with a subject S interposed therebetween. The image region designation device is provided in the radiological image processing device 3. The imaging control device 4 is connected to the radiation generation device 1, the radiation detector 2, the radiological image processing device 3, and the input unit 5, and the radiation detector 2 is connected to the radiological image processing device 3. In this embodiment, the images of distal portions of the human body, such as the patella, the nasal bone, and a finger, as diagnosis targets are captured. In the following description, the nasal bone is the diagnosis target.

The radiation generation device 1 includes a radiation tube 11 which emits radiation and a high voltage generator 12 which generates a tube voltage in the radiation tube 11 and can irradiate the subject S with radiation under the control of the imaging control device 4. The imaging control device 4 performs the setting of imaging conditions, such as the tube voltage, a tube current, and an irradiation time, and the control of operations based on the imaging conditions, on the basis of inputs from the input unit 5.

The radiation detector 2 stores radiological image information including radiation which has passed through the subject S as an electrostatic latent image and reads the stored electrostatic latent image to detect a radiation transmittance distribution as a radiological image. In addition, the radiation detector 2 may have any structure as long as it can detect radiation and output image information. For example, the radiation detector 2 may be a TFT-type solid-state detector or an optical-reading-type solid-state detector.

The radiological image processing device 3 is a computer including a high-definition liquid crystal display which displays, for example, images, a keyboard or a mouse (that is, the input unit 5) which receives inputs from an operator, and a main body having, for example, a CPU, a memory, a hard disk, and a communication interface, and has a function of performing various types of image processing including a gradation process for a radiological image.

The input unit 5 is an interface which includes, for example, a keyboard, a mouse, and a touch-panel-type input unit and receives various inputs required for the radiological image diagnosis system, such as an imaging instruction, an image processing instruction, and the designation of an imaging menu from the operator. In this embodiment, it is assumed that the touch-panel-type input unit is used.

Figure 2:
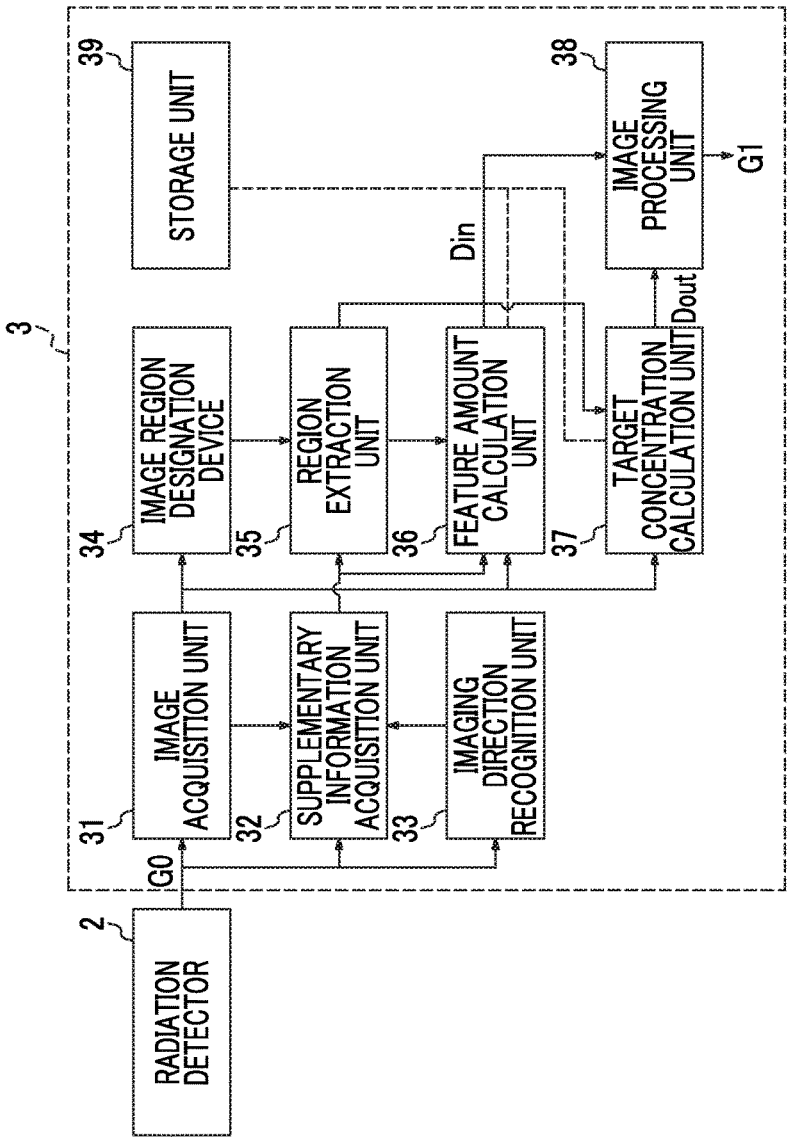
FIG. 2 is a block diagram schematically illustrating the structure of the radiological image processing device.

FIG. 2 is a block diagram schematically illustrating the structure of the radiological image processing device 3. As illustrated in FIG. 2, the radiological image processing device 3 includes an image acquisition unit 31, a supplementary information acquisition unit 32, an imaging direction recognition unit 33, an image region designation device 34 according to this embodiment, a region extraction unit 35, a feature amount calculation unit 36, a target concentration calculation unit 37, an image processing unit 38, and a storage unit 39.

The image acquisition unit 31 acquires a radiological image G0 acquired by the radiation detector 2 as digital data.

Figure 3:
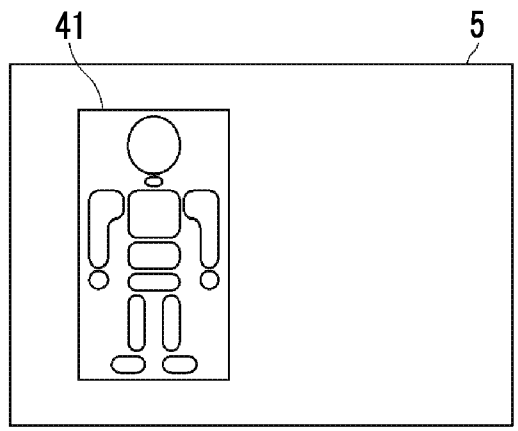
FIG. 3 is a diagram illustrating an interface which is related to the input of the part to be captured and is displayed on an input unit.

The supplementary information acquisition unit 32 acquires supplementary information H0 of the radiological image G0, such as a captured part of the subject S and an imaging direction. In this embodiment, the input unit 5 receives the supplementary information H0 input by the operator to acquire the captured part in the supplementary information H0. FIG. 3 is a diagram illustrating an interface which is related to the input of the captured part in the supplementary information H0 and is displayed on the input unit 5. As illustrated in FIG. 3, a simulated image 41 of the human body is displayed on the input unit 5. In the image 41, parts of the human body, such as the head, the neck, the chest, the abdomen, the waist, the upper limbs, the lower limbs, hands, and feet, are divided and displayed. For example, the operator touches and selects the captured part in the image 41 to input the captured part as the supplementary information H0. In this embodiment, since the nasal bone is used as the diagnosis target, the captured part is the head. The imaging direction is acquired by the imaging direction recognition unit 33 which will be described below. In this embodiment, it is assumed that both the captured part and the imaging direction are acquired as the supplementary information H0. However, any one of the captured part and the imaging direction may be acquired as the supplementary information H0.

The radiological image G0 may be analyzed to acquire the captured part. For example, the following method may be used: the captured radiological images of various parts are learned as teacher data, using machine learning, such as an adaptive boosting method; a discriminator for the captured parts is provided in the supplementary information acquisition unit 32; and the radiological image G0 is analyzed, using the discriminator, to acquire the captured parts as the supplementary information H0.

The imaging direction recognition unit 33 analyzes the radiological image G0 to acquire the imaging direction of the radiological image G0. For example, the following method may be used: the radiological images of various parts captured in the front direct, the lateral direction, and the axial direction (body axis direction) are learned as the teacher data, using machine learning, such as the adaptive boosting method; a discriminator for the captured part is provided in the supplementary information acquisition unit 32; and the radiological image G0 is analyzed, using the discriminator, to recognize the imaging direction. For example, the recognized imaging direction is used to calculate a target concentration which will be described. Therefore, the recognized imaging direction is input as a portion of the supplementary information H0 to the supplementary information acquisition unit 32. In this embodiment, since the nasal bone is used as a diagnosis target, the imaging direction is the front direction.

Figure 4:
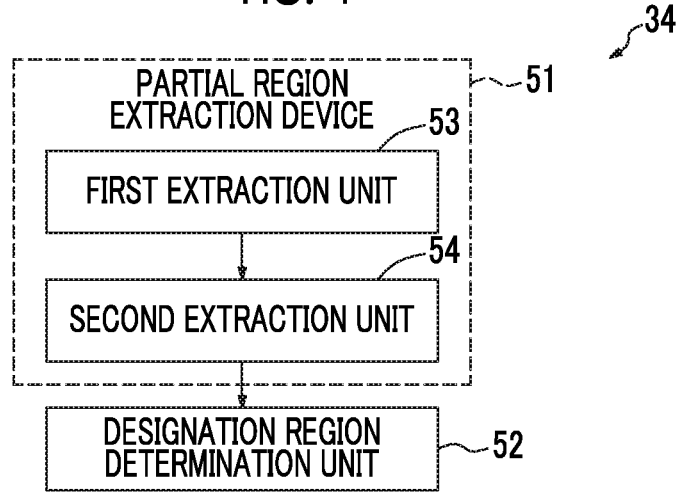
FIG. 4 is a block diagram schematically illustrating the structure of the image region designation device.

FIG. 4 is a block diagram schematically illustrating the structure of the image region designation device. As illustrated in FIG. 4, the image region designation device 34 includes a partial region extraction unit 51 and a designation region determination unit 52. The partial region extraction unit 51 includes a first extraction unit 53 and a second extraction unit 54. The first extraction unit 53 extracts at least one of a subject region and a void region included in the radiological image G0. As a method for extracting at least one of the subject region and the void region, for example, any known method can be used. For example, the method disclosed in JP2001-145614A can be used which performs a binarization process for the radiological image G0 to divide the radiological image G0 into the subject region obtained by the emission of radiation to the radiation detector 2 through the subject S and the void region obtained by the direct emission of radiation to the radiation detector 2.

Figure 5:
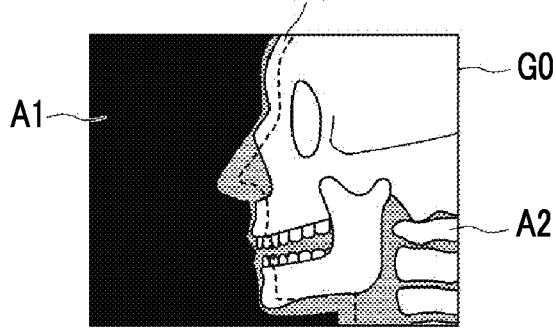
FIG. 5 is a diagram illustrating a radiological image having the nasal bone as a diagnosis target.

The second extraction unit 54 extracts a partial region in the vicinity of the boundary between the void region and the subject region in the subject region, on the basis of the extraction result of the first extraction unit 53. FIG. 5 is a diagram illustrating the extraction of the partial region. FIG. 5 illustrates a radiological image acquired by capturing the side image of the head of a person in order to observe the nasal bone. In this embodiment, the first extraction unit 53 divides the radiological image G0 into a void region A1 and a subject region A2 and extracts the void region A1. The second extraction unit 54 extracts a partial region A3 including a distal portion in the vicinity of the boundary between the void region A1 and the subject region A2. Here, the vicinity of the boundary means a predetermined range from the boundary. In this embodiment, the subject region A2 is reduced at a predetermined reduction ratio, using the center of gravity of the subject region A2 as the center, and a region which is surrounded by the contour of the reduced subject region and the contour of the subject region A2 (that is, a region in which the reduced subject region and the subject region A2 do not overlap each other) is extracted as the partial region A3. In this case, a region which is a predetermined distance away from the contour of the subject region A2 may be regarded as the partial region A3 or the subject region A2. In addition, the void region A1 may be enlarged at a predetermined enlargement ratio and a region which is surrounded by the contour of the enlarged void region and the contour of the subject region A2 may be extracted as the partial region A3.

In this case, the reduction ratio of the subject region A2 or the enlargement ratio of the void region A1 is set in advance according to supplementary information, such as the captured part and the imaging direction, and is stored in the storage unit 39. The second extraction unit 54 acquires information about the reduction ratio or the enlargement ratio from the storage unit 39, on the basis of the supplementary information H0 acquired by the supplementary information acquisition unit 32, and extracts the partial region. For example, a value of about 10% can be used as the reduction ratio or the enlargement ratio.

In addition, a region which extends a predetermined distance from the boundary between the void region A1 and the subject region A2 to the subject region A2 may be extracted as the partial region A3. In this case, for example, a value of about 2 cm can be used as the predetermined distance. In general, it is considered that a distance on the display device is used as a predetermined distance of 2 cm. However, the predetermined distance may be a distance on the actual image of the patient.

Figure 6:
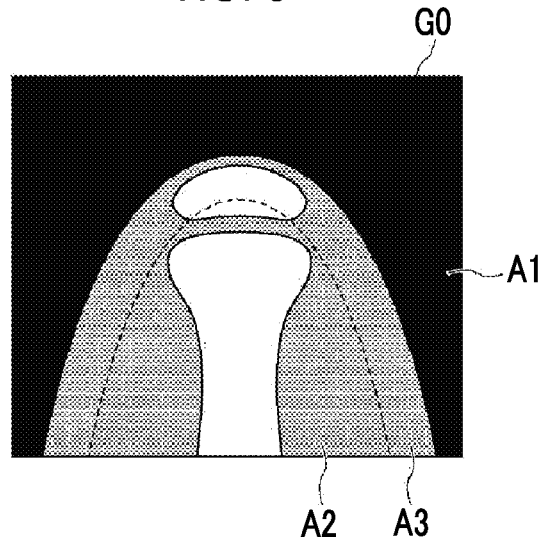
FIG. 6 is a diagram illustrating a radiological image having the patella as the diagnosis target.
Figure 7:
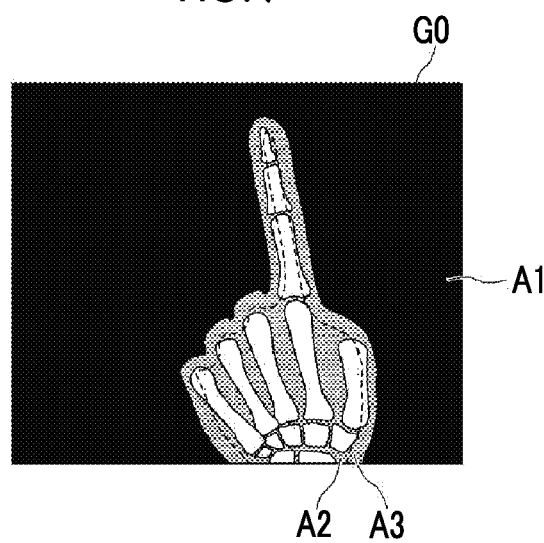
FIG. 7 is a diagram illustrating a radiological image having a finger as the diagnosis target.

For the partial region A3 including the distal portion, a distal portion other than the nasal bone can be extracted as the diagnosis target by the same method as described above. FIG. 6 is a diagram illustrating the extraction of a partial region when the patella is the diagnosis target and FIG. 7 is a diagram illustrating the extraction of a partial region when a finger is the diagnosis target. When any of the parts is used as the subject, the second extraction unit 54 extracts a partial region A3 including the distal portion in the vicinity of the boundary between a void region A1 and a subject region A2.

The designation region determination unit 52 determines at least one of the void region A1 and the partial region A3 extracted by the partial region extraction unit 51 as a designation region for designating the partial region A3. In this embodiment, both the void region A1 and the partial region A3 are determined as the designation region. After the designation region is determined, the radiological image G0 is displayed on the input unit 5 and the designated region of interest for calculating feature amounts, which will be described below, is received. At that time, the operator touches a desired portion of the radiological image G0 displayed on the input unit 5 to designate the region of interest. Then, when the designation region is designated, the partial region A3 is determined as the region of interest. When a region other than the designation region is designated, the designated region is determined as the region of interest. For example, when the subject region A2 is designated, the subject region A2 except for the partial region A3 or the subject region A2 including the partial region A3 is determined as the region of interest. In this embodiment, the input unit 5 is a touch panel type. However, for example, a cursor may be moved by a mouse or a keyboard to designate the region of interest.

The region extraction unit 35 extracts a bone part region and a soft part region from the region of interest determined by the instruction from the operator. In this embodiment, the bone part region and the soft part region are extracted from the partial region A3 since the diagnosis target is the nasal bone and the operator designates the designation region, that is, the partial region A3 as the region of interest. Here, the bone part region means a region of the radiological image G0 obtained by the emission of radiation to the radiation detector 2 through the subject S and the soft part region means a region of the radiological image G0 obtained by the emission of radiation to the radiation detector 2 through the tissues or organs other than the bone of the subject S. In general, a small amount of radiation transmits the bone part and the concentration of the image of the bone part is low (the brightness of the image is high). A large amount of radiation transmits the soft part and the concentration of the image of the soft part is high (the brightness of the image is low). The transmittance of radiation is lower than that in the void region.

Therefore, as a method for extracting the bone part region in the region extraction unit 35, any known method can be used. For example, the following method can be used: a method which extracts, as the bone part region, a region with a concentration that is equal to or less than a reference concentration from the subject region, using the fact that the concentration of the image of the bone part region is lower than the concentration of the image of the other regions, that is, the soft part region (the brightness of the image is higher than that of the image of the other regions); and the method for extracting the contour of the bone part which is disclosed in JP2010-253243A. In addition, as disclosed in JP4844560B, the bone part region may be extracted on the basis of, for example, the edge of the bone part included in the subject region by various types of image processing for skeletonization, such as a top hat process or a skeleton process, or an edge detection method using, for example, a Laplacian filter or a Sobel filter may be used. When a plurality of methods are used, the results of the plurality of methods may be added according to a predetermined weight. In this case, a method which determines how to add the results according to a neural network may be used. In addition, the region extraction unit 35 removes the extracted bone part region from the subject region to extract the soft part region.

The feature amount calculation unit 36 calculates a pixel value, which is a reference for a gradation process, as a feature amount Din from the radiological image G0. The reference pixel value means a pixel value which is converted into a target concentration Dout, which will be described below, by the gradation process. Hereinafter, the calculation of the feature amount Din will be described. In this embodiment, first, the feature amount calculation unit 36 determines the bone part region or the soft part region as a region (hereinafter, referred to as a usage region) which is used to calculate the feature amount Din. The usage region is determined on the basis of the supplementary information H0 acquired by the supplementary information acquisition unit 32 such that it is not a diagnosis target region to be diagnosed, but is a non-diagnosis target region which is not diagnosed.

In this embodiment, the diagnosis target is the nasal bone. In many cases, for example, this subject is used to diagnose a bone fracture and the state of the bone part is mainly observed for diagnosis. Therefore, the bone part region is likely to be the diagnosis target region. In this case, when the bone part region is determined as the usage region, the feature amount Din is determined using the region, of which the state, that is, the concentration is changed by the progress or healing of disease. Therefore, when the feature amount Din is converted into the target concentration Dout as described below, it is difficult to accurately reproduce a change in the concentration of the bone part region due to the progress or healing of disease on the processed radiological image. Therefore, when the bone part is in the diagnosis target region, the concentration of the image of the bone part does not change due to the progress or healing of disease and the soft part region which is a non-diagnosis target region is determined as the usage region.

When the operator wants to observe the soft part, such as the Achilles' tendon, the soft part is the diagnosis target region. In this case, the concentration of the image of the soft part does not change due to the progress or healing of disease and the bone part region which is a non-diagnosis target region, is determined as the usage region.

In this embodiment, a table T1 in which various captured parts and the usage regions are associated with each other may be made in advance and stored in the storage unit 39 and the region used to calculate the feature amount Din may be determined from information about the captured part, with reference to the table T1.

It may be determined which of the bone part region and the soft part region is used, according to the type of clinical department. For example, when the radiological image G0 of the chest is captured, an internist observes the state of the lung field and performs a diagnosis and an orthopedist observes the state of the ribs and performs a diagnosis. Therefore, even for the radiological image G0 of the same part, the diagnosis target region varies depending on the clinical department. Here, in a case in which the operator wants to observe the state of the lung field, when the soft part region is determined as the usage region, it is difficult to accurately reproduce a change in the state of the lung field on the processed radiological image. In a case in which the operator wants to observe the state of the bone part, when the bone part region is determined as the usage region, it is difficult to accurately reproduce a change in the state of the ribs on the processed radiological image.

Therefore, the supplementary information acquisition unit 32 may acquire the type of clinical department as the supplementary information H0 and may determine the usage region on the basis of the captured part and the type of clinical department. Specifically, when the clinical department is the internal department, the bone part region may be determined as the usage region in the captured radiological image G0 of the chest. When the clinical department is orthopedics, the soft part region may be determined as the usage region in the captured radiological image G0 of the chest. In this case, for the same radiological image of the chest, the internist can accurately observe the state of the lung field and the orthopedist can accurately observe the state of the ribs.

The user may designate the bone part region or the soft part region as the diagnosis target region.

Figure 8:
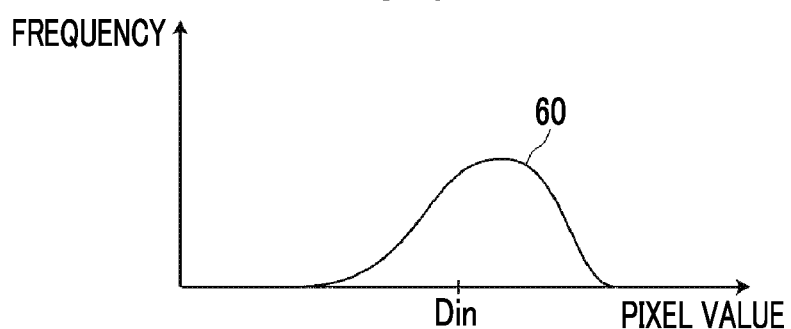
FIG. 8 is a diagram illustrating a histogram of a usage region and a calculated feature amount Din.

The feature amount calculation unit 36 makes a histogram of the pixel values in the determined usage region and calculates the feature amount Din on the basis of the histogram. In addition, the mean or median of the histogram, for example, a value which is in several percentages (for example, 20%) of the maximum concentration of the histogram can be used as the feature amount Din. FIG. 8 is a diagram illustrating the histogram of the usage region and the calculated feature amount Din. In FIG. 8, the median of a histogram 60 of the usage region is calculated as the feature amount Din.

It may be determined which of the values is used, on the basis of the supplementary information H0. For example, a table T2 in which various captured parts and various values of the histogram are associated with each other may be made in advance and stored in the storage unit 39. It may be determined which of the values of the histogram is used, on the basis of information about the captured part in the supplementary information H0, with reference to the table T2. Then, the feature amount Din may be calculated.

Figure 9:
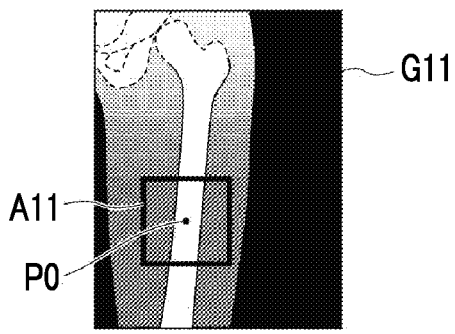
FIG. 9 is a diagram illustrating the positioning of a part including a buttock.

However, for example, when the image of the lower leg is captured, in some cases, the part including the buttock is positioned and the image thereof is captured. In this case, since the buttock is thicker than other parts, the concentration of the image of the buttock is lower than the concentration of the image of other soft parts in the same soft part region. Therefore, the distribution of the pixel values of the histogram in the soft part region is different when the part including the buttock is positioned and when the part without the buttock is positioned. As a result, the value of the feature amount Din is different in the two cases. For this reason, when the feature amount Din is calculated, the following method may be used: the position of the center of gravity of an irradiation field region or the subject region is calculated; the usage region is limited such that only the bone part region or the soft part region in a predetermined range from the position of the center of gravity is used; a histogram is calculated using only the pixel value in the limited usage region; and the feature amount Din is calculated. Here, the position of the center of gravity of the subject region is close to the center of the radiological image G0. Therefore, as illustrated in FIG. 9, in a radiological image G11 which is acquired by positioning the part including the buttock and capturing the image of the part, when the usage region is limited to a region A11 which is in a predetermined range from the position P0 of the center of gravity, the usage region for calculating the feature amount Din does not include the buttock. Therefore, it is possible to prevent the feature amount Din from varying due to a difference in positioning, even if the image of the same part is captured.

It is preferable that the distance from the position of the center of gravity changes depending on the captured part included in the supplementary information H0. In this case, a table T3 in which various captured parts are associated with the distance from the position of the center of gravity may be made in advance and stored in the storage unit 39, the distance from the position of the center of gravity may be determined on the basis of information about the captured part in the supplementary information H0, with reference to the table T3, and the feature amount Din may be calculated.

Figure 10:
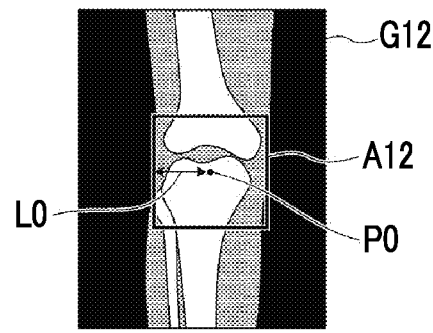
FIG. 10 is a diagram illustrating a radiological image of the knee joint.

In addition, the shortest distance from the position of the center of gravity of the subject region to a region outside the subject may be calculated and the histogram may be calculated using only the pixel values in the bone part region or the soft part region which is in the range of the shortest distance as a reference distance. For example, as illustrated in FIG. 10, in a radiological image G12 of the knee joint, the shortest distance L0 from the position P0 of the center of gravity to a region outside the subject may be calculated and a square region A12 having one side with a length of 2L0 may be limited to the usage region. When an imaging process is performed using an irradiation field diaphragm, the position of the center of gravity of the irradiation field region may be used as the position of the center of gravity of the subject region.

In some cases, the image of a fixing tool for fixing a target region during imaging or the image of an artifact, such as an artificial joint, is included in the radiological image G0. The artifact appears as a region with low concentration (high brightness) in the radiological image. Therefore, when the artifact is included in the usage region, the histogram oscillates toward the low concentration side, which makes it difficult to stably calculate the feature amount Din even if the same part is captured. For this reason, a region with low concentration is extracted as an artifact from the subject region. When an artifact is included in the usage region, the artifact or the artifact and a region in the vicinity of the artifact are removed from the usage region. In this case, it is possible to stably calculate the feature amount Din, without being affected by the artifact.

Figure 11:
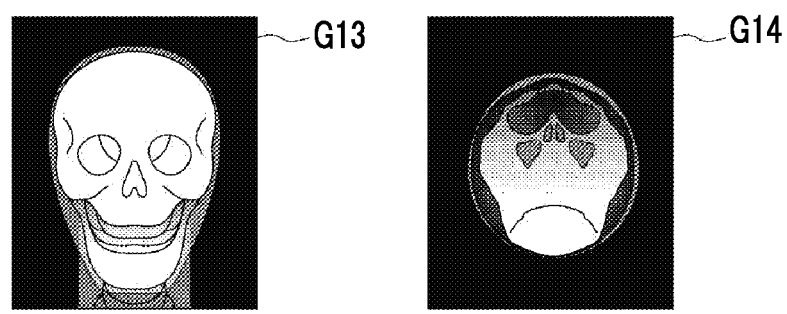
FIG. 11 is a diagram illustrating a radiological image of the head

The target concentration calculation unit 37 calculates a target concentration Dout which is a target concentration of the feature amount Din. Hereinafter, the calculation of the target concentration Dout will be described. FIG. 11 is a diagram illustrating the front and axial radiological images of the head. As illustrated in FIG. 11, in a radiological image G13 which is captured in the front direction, the thickness of the bone part region is substantially uniform in the substantially entire subject region. Therefore, the concentration of the entire subject region is relatively low and the concentration of an eye socket region is relatively low. In contrast, in a radiological image G14 which is captured in the axial direction, the thickness of the bone part region is not uniform in each pixel. Therefore, the bone part region includes a region with low concentration and a region with high concentration and the concentration of the eye socket region is relatively high. When the same part is captured and a gradation process is performed with the same target concentration Dout, the feature amount Din calculated from the bone part region and a difference in the concentration of the eye socket are different. Therefore, it is difficult to optimize the quality of the processed radiological image according to the imaging direction.

Therefore, in this embodiment, the target concentration calculation unit 37 determines the direction in which the radiological image G0 has been captured from the front direction, the lateral direction, and the axial direction (body axis direction) of the subject S, on the basis of information about the imaging direction recognized by the imaging direction recognition unit 33, and calculates the target concentration Dout according to the imaging direction. In this embodiment, a table T4 in which various imaging directions are associated with the target concentration Dout is stored in the storage unit 39 and the target concentration calculation unit 37 calculates the target concentration Dout from the information about the imaging direction, with reference to the table T4. In this embodiment, since the subject is the nasal bone, the target concentration calculation unit 37 calculates the target concentration Dout from the imaging direction (that is, the side of the head), with reference to the table T4.

The target concentration calculation unit 37 may calculate the target concentration Dout on the basis of the shape of the subject region extracted by the image region designation device 34. For example, when the image of the head is captured, the shape of the subject region is close to a circle. That is, as the degree of circularity increases, the imaging direction is closer to the axial direction. Therefore, the following method may be used: the degree of circularity of the subject region is calculated; a table T5 in which the degree of circularity of the subject region is associated with the target concentration Dout is stored in the storage unit 39; and the target concentration Dout is calculated from the shape of the subject region with reference to the table T5.

For the captured part other than the head, the shape of the subject S is a characteristic element which varies depending on the imaging direction. Therefore, the following method may be used: a shape degree indicating the degree of shape of the subject region is calculated; a table in which the shape degree of the subject region is associated with the target concentration Dout is stored in the storage unit 39; and the target concentration Dout is calculated from the shape of the subject region with reference to the table.

The target concentration Dout may be calculated on the basis of the distribution of the bone part region extracted by the region extraction unit 35. For example, when the radiological image G0 of the head is captured, the bone part region is distributed over the substantially entire subject region in the case of the radiological image G13 which is captured in the front direction as illustrated in FIG. 11 and a thick bone part region is largely distributed on the lower side of the subject region in the case of the radiological image G14 captured in the axial direction. Therefore, a table T6 in which the distribution state of various bone part regions in the subject region is associated with the target concentration Dout for each captured part may be stored in the storage unit 39 and the target concentration Dout may be calculated from the distribution of the bone part region with reference to the table T6.

When the radiological image G0 of the head is captured, the ratio of the area of the bone part region with low concentration to the area of the subject region is high, as illustrated in FIG. 11. Therefore, it is possible to specify the imaging direction on the basis of the ratio of the area of the bone part region with low concentration to the area of the subject region. The target concentration Dout may be calculated on the basis of the ratio of the area of the bone part region with low concentration to the area of the subject region. In this case, a table T7 in which various ratios of the area of the bone part region to the area of the subject region are associated with the target concentration Dout for each captured part may be stored in the storage unit 39 and the target concentration Dout may be calculated from the ratio of the area of the bone part region to the area of the subject region with reference to the table T7.

Figure 12:
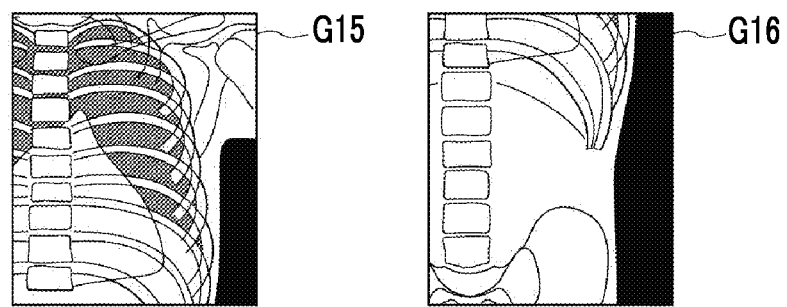
FIG. 12 is a diagram illustrating a radiological image of the chest.

When the image of the chest is captured, the region extraction unit 35 may extract a lung field region as an anatomic region and the target concentration Dout may be calculated on the basis of the distribution of the lung field region. FIG. 12 is a diagram illustrating the captured radiological image of the chest, particularly, the radiological image of the upper ribs and the radiological image of the lower ribs. As illustrated in FIG. 12, in a captured radiological image G15 of the upper ribs, the lung field region is distributed over the entire subject region in the vertical direction. In contrast, in a captured radiological image G16 of the lower ribs, the lung field region is distributed on the upper side of the subject region. Therefore, when the image of the lower ribs is captured, the area of a tissue region of the abdomen in the subject region is larger than that when the image of the upper ribs is captured. As a result, the concentration of the image of the entire subject region is low. For this reason, when a gradation process is performed for the same captured image including the upper ribs and the lower ribs with the same target concentration Dout, it is difficult to optimize the concentration and contrast of the ribs in the processed radiological image according to the captured part. Therefore, a table T8 in which various distributions of the lung field region are associated with the target concentration Dout may be stored in the storage unit 39 and the target concentration Dout may be calculated from the distribution of the lung field region with reference to the table T8. Any known method can be used to extract the lung field region. For example, a method can be used which performs a binarization process to divide the soft part region into an air region and a soft part tissue region and extracts the lung field region.

The lung field region is distributed in the vertical direction of the radiological image of the upper ribs and is present only in the upper part of the radiological image of the lower ribs. Therefore, it is possible to recognize whether the radiological image of the upper ribs or radiological image of the lower ribs is captured from the distribution of the lung field region. A table T9 in which the captured part is associated with the target concentration Dout may be stored in the storage unit 39 and the target concentration Dout may be calculated from the recognized captured part on the basis of the distribution of the lung field region, with reference to the table T9.

A method for calculating the target concentration Dout is not limited to the above-mentioned method and any known method can be used. In addition, the target concentration Dout may be calculated by a combination of the above-mentioned various methods.

Figure 13:
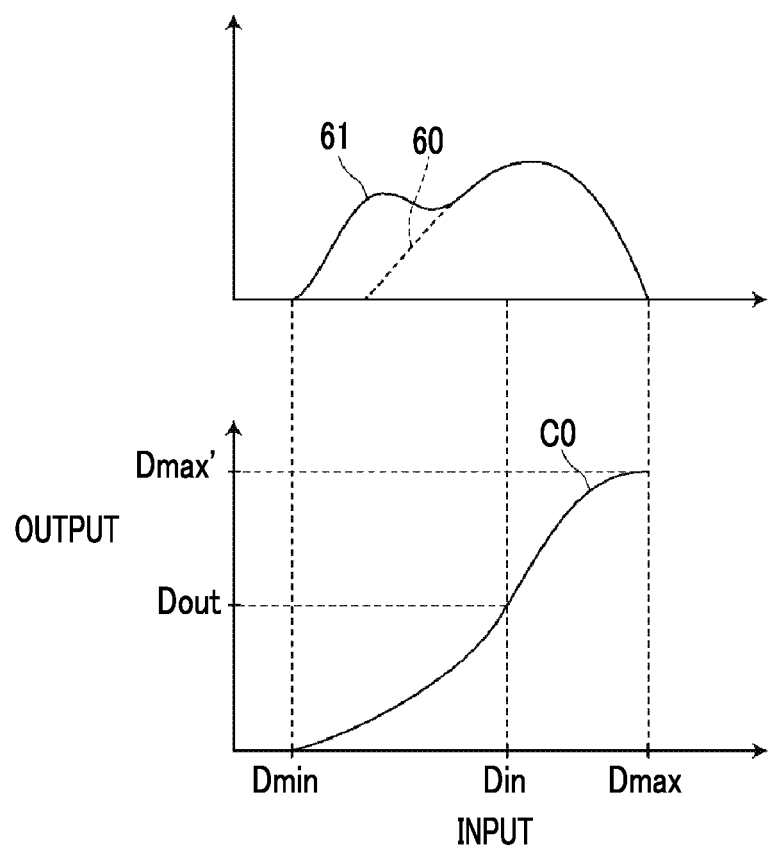
FIG. 13 is a diagram illustrating the setting of a gradation curve.

The image processing unit 38 sets a gradation curve such that the feature amount Din is the target concentration Dout. FIG. 13 is a diagram illustrating the setting of the gradation curve. In FIG. 13, a histogram 61 of the subject region is represented by a solid line and the histogram 60 of the usage region (here, the soft part region) used to calculate the feature amount Din is represented by a dashed line. First, the image processing unit 38 determines the minimum concentration Dmin and the maximum concentration Dmax of the subject region. The minimum concentration Dmin and the maximum concentration Dmax are the minimum value and the maximum value on the horizontal axis (that is, the pixel value) of the histogram 61 of the subject region, respectively. Then, the image processing unit 38 sets a gradation curve C0 such that the feature amount Din calculated by the feature amount calculation unit 36 is the target concentration Dout calculated by the target concentration calculation unit 37 and the maximum concentration Dmax is the maximum concentration Dmax' of a processed radiological image G1 from an output device (for example, a display device), as illustrated in FIG. 13.

Then, the image processing unit 38 converts the gradation of the radiological image G0, using the set gradation curve. In addition, the image processing unit 38 performs other types of image processing, such as frequency processing and a graininess suppression process, to acquire the processed radiological image G1.

Figure 14:
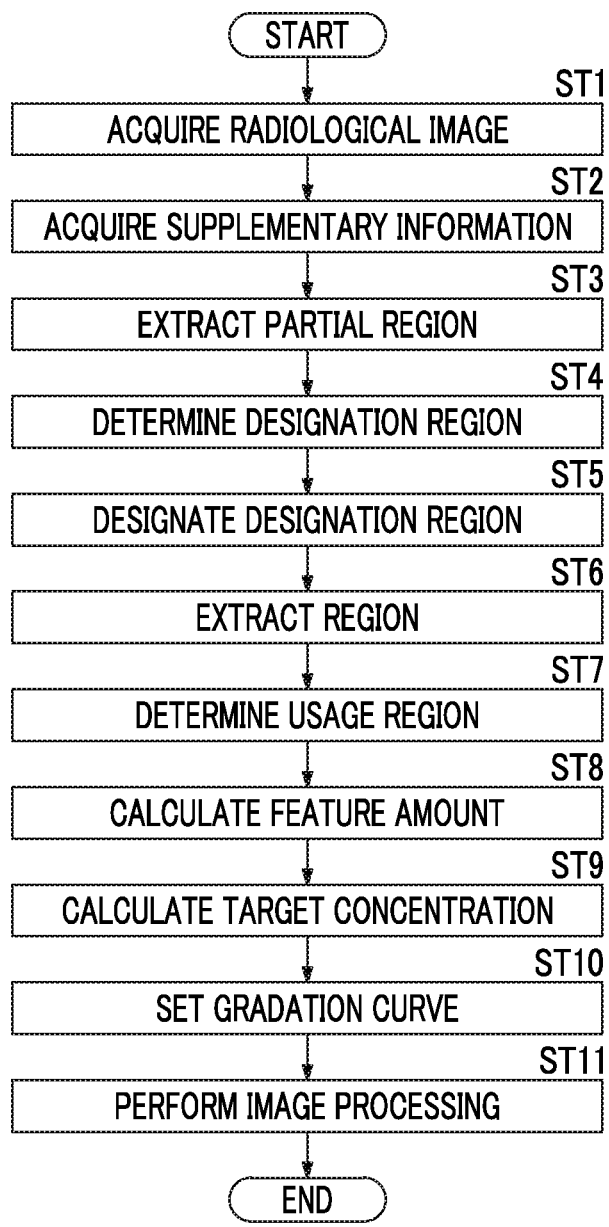
FIG. 14 is a flowchart illustrating a process performed in this embodiment.

Next, a process which is performed in this embodiment will be described. FIG. 14 is a flowchart illustrating the process performed in this embodiment. It is assumed that the image of the subject S has been captured. First, the image acquisition unit 31 acquires the radiological image P0 from the radiation detector 2 (Step ST1) and the supplementary information acquisition unit 32 acquires the supplementary information H0 of the radiological image G0 (Step ST2).

Then, the partial region extraction unit 51 of the image region designation device 34 extracts the partial region A3 (Step ST3) and the designation region determination unit 52 determines a designation region for designating the partial region A3 (Step ST4). Then, when the operator designates the region of interest for calculating the feature amounts as the designation region (Step ST5), the region extraction unit 35 extracts the bone part region and the soft part region from the partial region A3 (region extraction: Step ST6) and the feature amount calculation unit 36 determines a usage region used to calculate the feature amount Din (Step ST7) and calculates the feature amount Din from the determined region (Step ST8). The target concentration calculation unit 37 calculates the target concentration Dout for converting the feature amount Din (Step ST9) and the image processing unit 38 sets the gradation curve C0 such that the feature amount Din is the target concentration Dout (Step ST10). In addition, the image processing unit 38 performs image processing including a gradation process using the gradation curve C0 for the radiological image G0 and acquires a processed radiological image G1 (Step ST11). Then, the process ends.

As such, in this embodiment, the partial region A3 including the distal portion in the vicinity of the boundary between the subject region A2 and the void region A1 is extracted and at least one of the void region A1 and the partial region A3 is determined as the designation region for designating the partial region A3. Therefore, it is possible to designate the partial region A3 including the distal portion, using the designation region that is wider than the distal portion. As a result, when a desired distal portion is designated, it is possible to prevent another region from being erroneously designated and thus to accurately designate the desired distal portion.

In this embodiment, the feature amount Din is calculated on the basis of the partial region A3 including the distal portion and the target concentration Dout for converting the feature amount Din is calculated on the basis of the radiological image G0. Then, the gradation process is performed for the radiological image G0 such that the feature amount Din is the target concentration Dout. Therefore, it is not necessary to set the imaging menu in detail and it is possible to optimize the quality of the processed radiological image G1 including the distal portion, particularly, the concentration and contrast of the processed radiological image G1, while reducing the number of imaging menus to be set.

The imaging direction is recognized on the basis of the radiological image G0 and target concentration is calculated on the basis of the recognized imaging direction. Therefore, it is possible to omit the setting of the imaging menu related to the imaging direction.

In addition, an anatomic region, such as a bone part region, a soft part region, or a lung field region, is extracted from the radiological image G0 and the target concentration Dout is calculated on the basis of at least one of the position, size, and distribution of the anatomic region. Therefore, it is possible to omit the setting of the imaging menu related to at least one of the position, size, and distribution of the anatomic region.

Of the bone part region and the soft part region, a non-diagnosis region which is not a diagnosis target is determined as the usage region used to calculate the feature amount Din. Therefore, it is possible to calculate the feature amount Din, using the region of which the state does not change over time or depending on disease. As a result, it is possible to appropriately reproduce a change in the state of a diagnosis target region due to the progress or healing of disease on the processed radiological image G1.

In the above-described embodiment, the void region A1 and the partial region A3 are determined as the designation region. However, only the void region A1 or only the partial region A3 may be determined as the designation region. When a distal portion of the human body is a diagnosis target, the size of the void region A1 increases in the radiological image G0. Therefore, when only the void region A1 is determined as the designation region, it is possible to accurately and easily designate the distal portion.

In the above-described embodiment, the target concentration Dout is determined from the radiological image G0. However, the target concentration Dout which is determined in advance may be used.

In the above-described embodiment, the feature amount calculation unit 36 determines the usage region used to calculate the feature amount Din. However, in some cases, when the feature amount Din is calculated from the determined usage region, the quality of the processed radiological image G1 is not stable. For example, since the radiological image including a distal portion of the human body, such as the nasal bone, the patella, a finger, a hand, or a foot, is captured in order to diagnose the bone part, a diagnosis region is the bone part. Therefore, according to this embodiment, the region used to calculate the feature amount Din is determined to be the soft part region which is a non-diagnosis region. However, the range of the soft part region is narrow in the distal portion. Therefore, when the feature amount Din is calculated using the histogram of the soft part region, the feature amount Din is not stable. As a result, the quality of the processed radiological image G1 is not stable.

Therefore, the image region designation device 34 may determine whether the proportion of the area of the extracted subject to the radiological image G0 is less than a predetermined value. When the determination result is "Yes", the region used to calculate the feature amount Din may be determined as the bone part region. In addition, the region to be used to calculate the feature amount Din may be determined on the basis of the areas of the bone part region and the soft part region. For example, when the bone part is a diagnosis target region, the soft part region is determined as the region used to calculate the feature amount Din. When the area of the soft part region is small, the region used to calculate the feature amount Din may switch to the bone part region. A portion of the subject region may be recognized and the bone part region may be determined as the region used to calculate the feature amount Din when the recognized portion is a distal portion, such as a finger, a hand, or a foot.

In the above-described embodiment, the bone part region and the soft part region are extracted from the subject region and are determined as the region used to calculate the feature amount Din. However, when the image of the breast is captured, there is no bone part region. Therefore, the subject region may be divided into a mammary gland region and a fat region in the captured radiological image G0 of the breast. Here, in the case of the breast, since the diagnosis target region is the mammary gland region, the region used to calculate the feature amount Din is preferably the fat region.

In the above-described embodiment, of the bone part region and the soft part region, a non-diagnosis target region is determined as the region used to calculate the feature amount Din. However, the invention is not limited thereto. The diagnosis target region to be diagnosed may be determined as the region used to calculate the feature amount Din.

In the above-described embodiment, the radiation detector 2 is used to acquire the radiological image of the subject S. However, the radiological image may be acquired using a stimulable phosphor sheet which stores a portion of radiation energy obtained by the irradiation of radiation and emits stimulable light corresponding to the stored radiation energy when being irradiated with excitation light such as visible light or laser light. When the stimulable phosphor sheet is used, the stimulable phosphor sheet is irradiated with radiation which has passed through the subject and radiological image information is stored and recorded on the stimulable phosphor sheet. Then, when the storage phosphor sheet is irradiated with excitation light, stimulable light is emitted and is then converted into an electric signal to acquire the radiological image.

What is claimed is:
1. A radiological image processing device that designates a region in a radiological image including a distal portion of a human body, comprising:

a memory configured to store instructions; and a processor configured to execute the stored instructions, which when executed by the processor cause the processor to:

extract a partial region which includes the distal portion and has a predetermined range from a boundary between a subject region and a void region from the radiological image; and determine at least one of the void region or the region including both the void region and the partial region as a designation region for designating the partial region, calculate a feature amount which is a concentration of the radiological image based on the partial region when the designation region is designated;

calculate a target concentration which is converted from the feature amount by determining a thickness of the subject region, and perform image processing such that the calculated feature amount is the calculated target concentration, wherein, when the designation region is designated on the radiological image being displayed, the partial region is designated.

2. The radiological image processing device according to claim 1, wherein the processor is further configured to determine the void region and the partial region as the designation region.

3. The radiological image processing device according to claim 1, wherein the processor is further configured to determine the void region as the designation region.

4. The radiological image processing device according to claim 1, wherein the processor is further configured to:

extract at least one of the subject region and the void region from the radiological image; and extract the partial region on the basis of at least one of the subject region and the void region.

5. The radiological image processing device according to claim 1, further comprising:

an input interface configured to receive the designation region, wherein the determining the thickness of the subject region comprises determining a direction in which the radiological image was captured, and wherein the image processing comprises a gradation process for the radiological image.

6. The radiological image processing device according to claim 3, wherein the processor is further configured to:

extract a bone part region or a soft part region included in the radiological image as an anatomic region from the partial region, and calculate the feature amount based on the bone part region or the soft part region.

7. A radiological image processing method in which a region in a radiological image including a distal portion of a human body is designated, the method comprising:

extracting, by a processor, a partial region which includes the distal portion and has a predetermined range from a boundary between a subject region and a void region from the radiological image;

determining, by the processor, at least one of the void region or the region including both the void region and the partial region as a designation region for designating the partial region;

calculating, by the processor, a feature amount which is a concentration of the radiological image based on the partial region when the designation region is designated;

calculating, by the processor, a target concentration which is converted from the feature amount by determining a thickness of the subject region, and performing, by the processor, image processing such that the calculated feature amount is the calculated target concentration, wherein, when the designation region is designated on the displayed radiological image, the partial image is designated.

8. The method of claim 7, wherein the determining the thickness of the subject region comprises determining a direction in which the radiological image was captured, and wherein the performing of the image processing comprises a gradation process for the radiological image.

9. A non-transitory recording medium having a program recorded therein that causes a computer to execute a radiological image processing comprising image region designation method that designates a region in a radiological image including a distal portion of a human body recorded therein, the program comprising the procedures of:

extracting a partial region which includes the distal portion and has a predetermined range from a boundary between a subject region and a void region from the radiological image;

determining at least one of the void region or the region including both the void region and the partial region as a designation region for designating the partial region;

calculating a feature amount which is a concentration of the radiological image based on the partial region when the designation region is designated;

calculating a target concentration which is converted from the feature amount by determining a thickness of the subject region, and perform image processing such that the calculated feature amount is the calculated target concentration, wherein, when the designation region is designated on the displayed radiological image, the partial region is designated.

10. The non-transitory recording medium according to claim 9, wherein the determining the thickness of the subject region comprises determining a direction in which the radiological image was captured, and wherein the image processing comprises a gradation process for the radiological image.

* * * * *